United States Patent
Hernandez

(10) Patent No.: US 7,994,385 B2
(45) Date of Patent: Aug. 9, 2011

(54) ABSORBENT ARTICLE INCLUDING ABSORBENT CORE HAVING CONCENTRICALLY ARRANGED ABSORBENT REGIONS

(75) Inventor: Francisco J. V. Hernandez, São José dos Campos (BR)

(73) Assignee: Johnson & Johnson Ind. E Com. Ltda (BR)

( * ) Notice: Subject to any disclaimer, the term of this patent is extended or adjusted under 35 U.S.C. 154(b) by 323 days.

(21) Appl. No.: 12/185,892

(22) Filed: Aug. 5, 2008

(65) Prior Publication Data

US 2010/0036343 A1    Feb. 11, 2010

(51) Int. Cl.
    *A61F 13/15*    (2006.01)
(52) U.S. Cl. ............... 604/378; 604/385.101; 604/380; 604/379; 604/375; 604/374
(58) Field of Classification Search .............. 604/378, 604/385.101, 380, 379, 375, 374
    See application file for complete search history.

(56) References Cited

U.S. PATENT DOCUMENTS

| 4,834,735 | A  |   | 5/1989  | Alemany et al. |
| 5,047,023 | A  | * | 9/1991  | Berg ........................ 604/368 |
| 6,037,518 | A  |   | 3/2000  | Guidotti et al. |
| 6,503,234 | B1 |   | 1/2003  | Canuel et al. |
| 6,673,982 | B1 |   | 1/2004  | Chen et al. |
| 2005/0109442 | A1 |   | 5/2005 | Neubauer |

FOREIGN PATENT DOCUMENTS

| EP | 1371348 A | 12/2003 |
| WO | WO 97/19659 A | 6/1997 |
| WO | WO 02/068002 A | 9/2002 |
| WO | WO 2004/011723 A | 2/2004 |
| WO | WO 2006/105305 A | 10/2006 |
| WO | WO 2007/008124 A | 1/2007 |

* cited by examiner

*Primary Examiner* — Jacqueline F Stephens

(57) ABSTRACT

The absorbent article according to the present invention includes a laminate structure including cover, transfer layer, core and barrier, the absorbent core having a first central region and second region concentrically surrounding the first region.

7 Claims, 10 Drawing Sheets

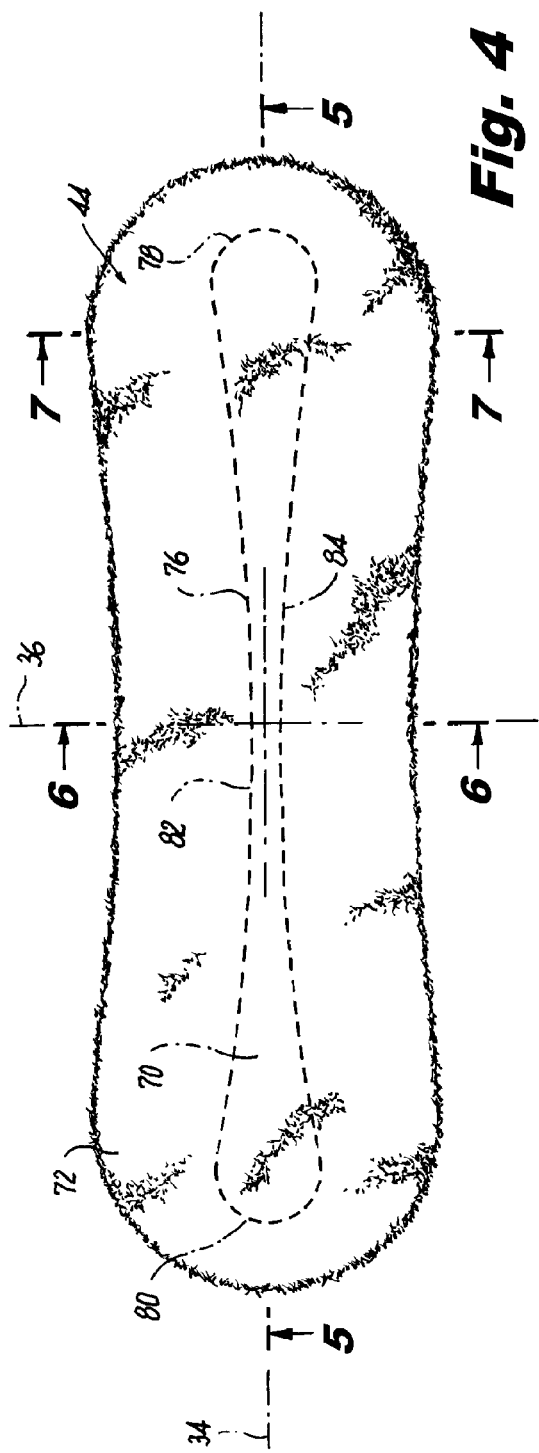
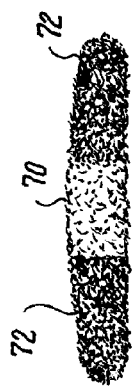
Fig. 4
Fig. 5
Fig. 6
Fig. 7

ABSORBENT ARTICLE INCLUDING ABSORBENT CORE HAVING CONCENTRICALLY ARRANGED ABSORBENT REGIONS

FIELD OF THE INVENTION

The present invention generally relates to sanitary absorbent articles and in particular to feminine sanitary absorbent napkins having enhanced body confirmation and superior fluid handling characteristics.

BACKGROUND OF THE INVENTION

Externally worn, sanitary absorbent napkins are one of many kinds of feminine protection devices currently available. The development of materials having a high liquid absorption capacity per unit volume has allowed the required overall thickness of sanitary napkins to be reduced, thereby providing a product which is more comfortable and less obtrusive to wear. Sanitary napkins of this type, i.e. napkins having a thickness of less than five millimeters, are commonly referred to "ultrathin" sanitary napkins and conventionally have a laminate construction including a body-facing liquid permeable layer, an absorbent core layer or layers, and a liquid impermeable garment facing layer. Due to the laminate construction of a conventional ultrathin napkins, and the relatively high density of some of the constituent layers thereof, ultrathin napkins do not readily conform to the contours of the body. Rather, such napkins tend to fold rather than conform to the body, thereby leaving gaps between the body and the body-facing surface of the napkin. These gaps can lead to leakage of menstrual fluid before the napkin has an opportunity to absorb the same. In addition, the tendency of an ultrathin napkin to fold during use can cause discomfort to these user at those locations where the user's body comes in contact with the folded portions of the napkin.

The inventors of the present invention have discovered a sanitary napkin construction that overcomes the shortcomings of ultrathin sanitary napkins described above and more particularly a napkin that provides enhanced body confirmation and superior fluid handling characteristics.

SUMMARY OF THE INVENTION

In view of the foregoing, the present invention provides an absorbent article including a liquid pervious cover layer, a liquid impervious barrier layer, an absorbent core arranged between the cover layer and barrier layer, a transfer layer arranged between the cover layer and the core, a longitudinal centerline, a transverse centerline, the absorbent core having a first region and second region concentrically surrounding the first region, the first region having a first basis weight and the second region having a second basis weight, the first basis weight being less than the second basis weight, the first basis weight being in the range of between 7.5 gsm and 385 gsm and the second basis weight being in the range of between 150 gsm and 450 gsm, the basis weight of the first region being about 5% to about 85% the basis weight of the second region, and wherein the first region includes a first end portion located on a first side of the transverse centerline and a second end portion located on an opposite side of the transverse centerline.

BRIEF DESCRIPTION OF THE DRAWINGS

Examples of embodiments of the present invention will now be described with reference to the drawings, in which:

FIG. 4 is a top plan view of the core layer of the sanitary napkin shown in FIG. 1 showing the first and second concentric regions thereof;

FIG. 5 is a sectional view taken along line 5-5 in FIG. 4;

FIG. 6 is a sectional view taken along line 6-6 in FIG. 4;

FIG. 7 is a sectional view taken along line 7-7 in FIG. 4;

DETAILED DESCRIPTION OF THE INVENTION

Figure 1:
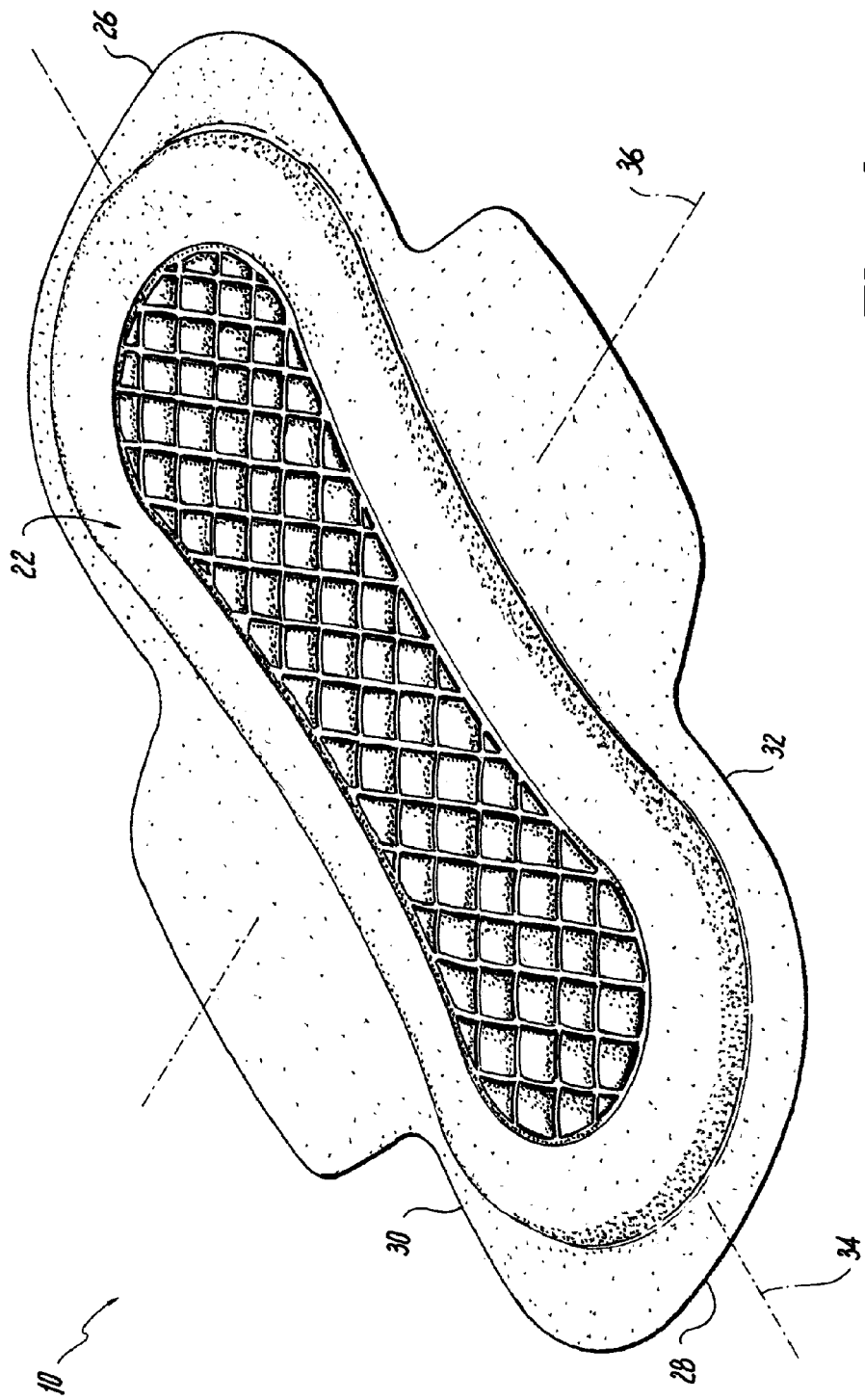
FIG. 1 is a perspective view of a sanitary napkin in accordance with an embodiment of the present invention.
Figure 2:
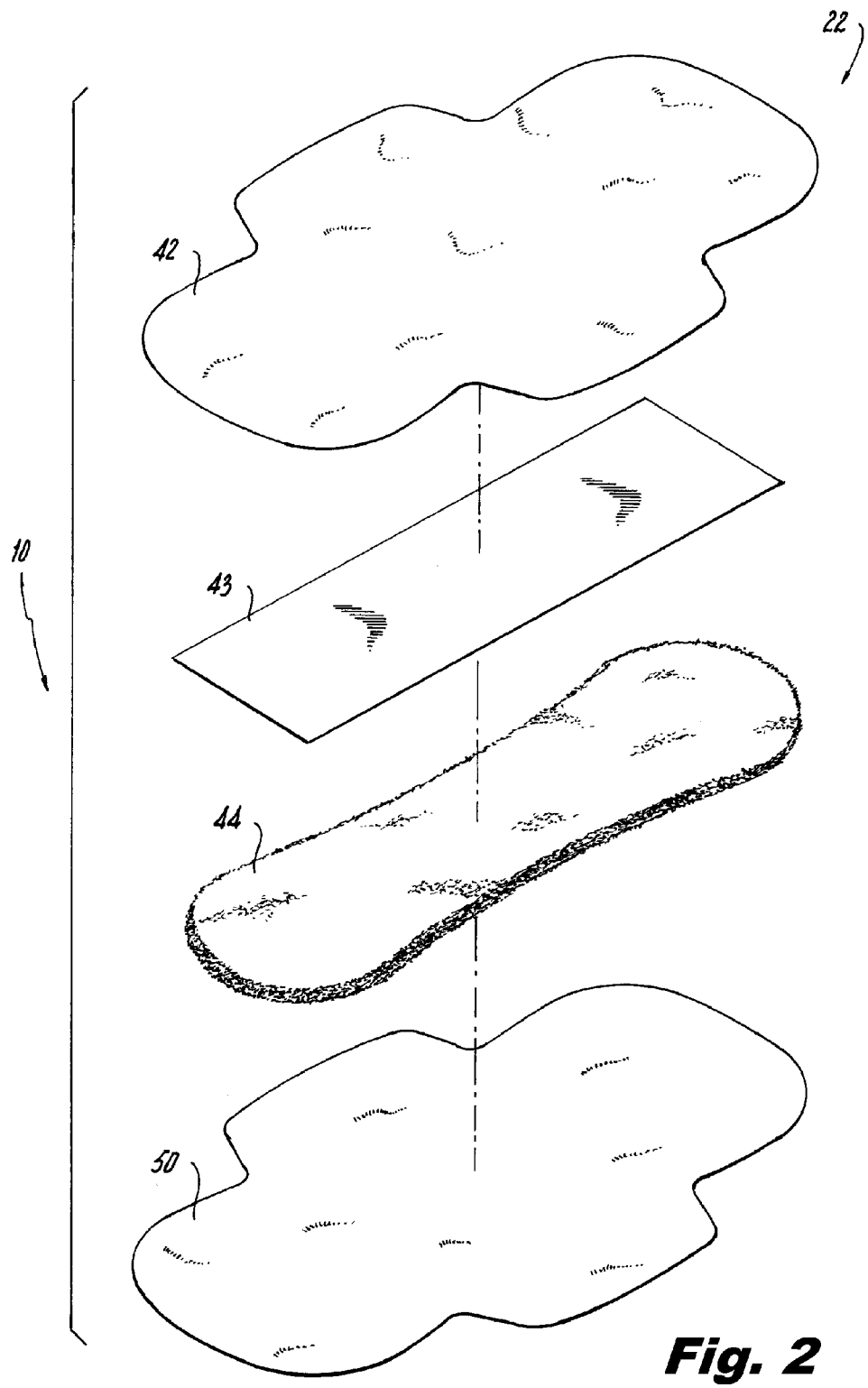
FIG. 2 is an exploded view of the sanitary napkin shown in FIG. 1, according to a first embodiment of the invention, showing the constituent layers thereof.

Referring to FIGS. 1 and 2, there is shown an embodiment of the present invention, a feminine sanitary napkin 10.

The sanitary napkin 10 has a main body 22 with a first transverse side 26 defining a front portion thereof and a second transverse side 28 defining a rear portion thereof. The main body also has two longitudinal sides, namely a longitudinal side 30 and a longitudinal side 32. The sanitary napkin 10 preferably has a thickness less than 5 mm, more preferably less than 4 mm, and most preferably less than 3.5 mm according to the test method set forth herein ("Procedure for Measuring the Thickness of an Absorbent Article").

The sanitary napkin 10 has a longitudinal centerline 34 that is an imaginary line bisecting the sanitary napkin 10 in two identical halves. The main body 22 also has an imaginary transverse centerline 36 perpendicularly arranged relative to the longitudinal centerline 34.

As depicted in FIG. 2, the main body 22, according to a first embodiment of the invention, is of a laminate construction and includes a fluid-permeable cover layer 42, a transfer layer 43, an absorbent core 44 and a fluid-impervious barrier layer 50.

Figure 3:
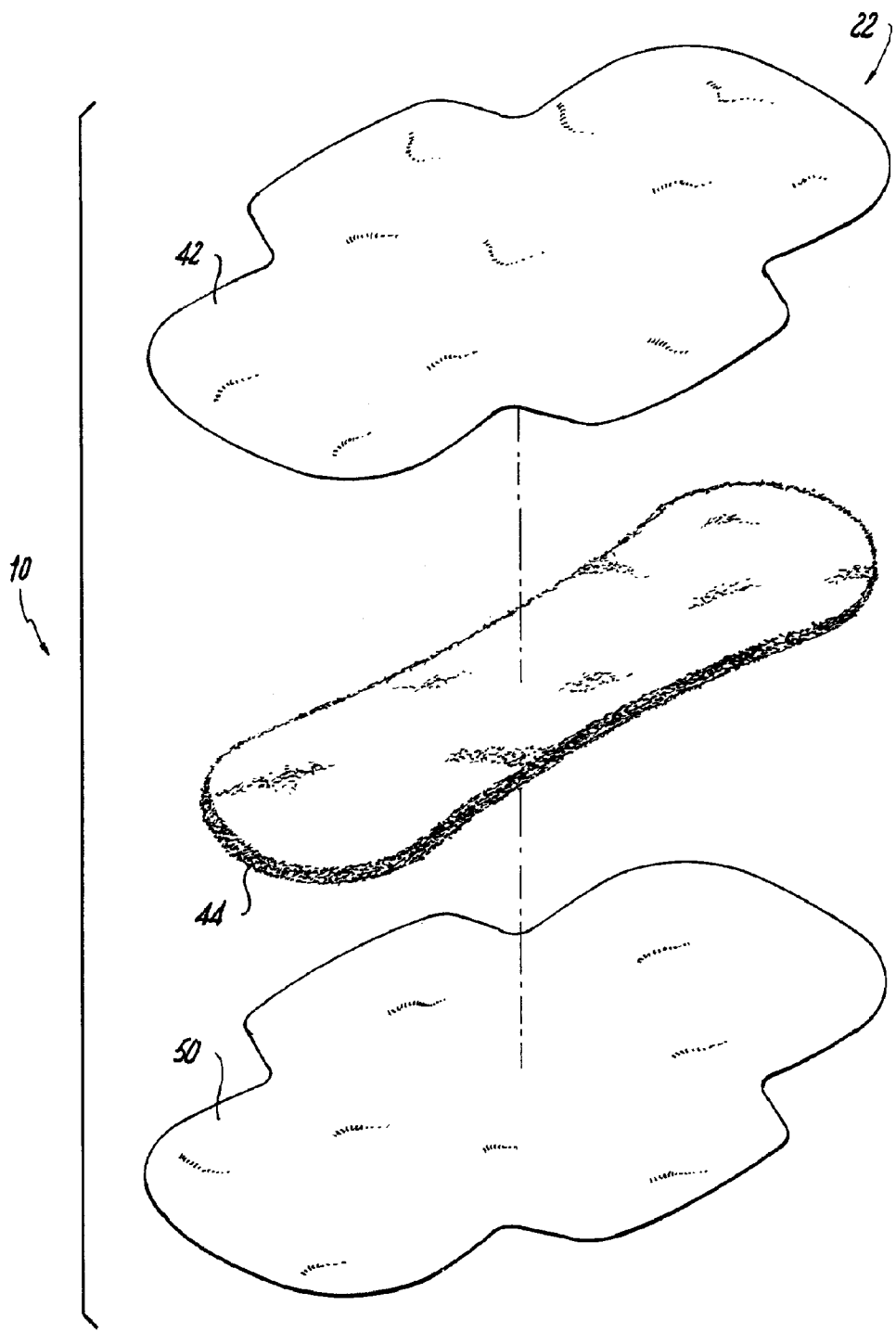
FIG. 3 is an exploded view of the sanitary napkin shown in FIG. 1, according to a second embodiment of the invention, showing the constituent layers thereof.

As depicted in FIG. 3, the main body 22, according to a second embodiment of the invention, is of a laminate construction and includes a fluid-permeable cover layer 42, an absorbent core 44, and a fluid-impervious barrier layer 50.

Referring to FIGS. 4-7, the absorbent core 44 includes a first region 70 and second region 72 concentrically surrounding the first region 70. The first region 70 has a basis weight in the range of between 7.5 gsm (g/m$^2$) and 385 gsm (g/m$^2$) and the second region 72 have a basis weight in the range of between 150 gsm and 450 gsm. The basis weight of the first region 70 is selected such that is less than the basis weight of the second region 72. In particular, the basis weight of the first region 70 is selected such that it is has a basis weight of about 5% to about 85% the basis weight of the second region 72.

As shown in FIG. 4 the first region 70 extends along the longitudinally extending centerline 34 of the sanitary napkin 10 and is arranged symmetrically with respect to the longitudinally extending centerline 34. Preferably the first region 70 extends over about 5% to about 30% the surface area of the core 44 and the second region 72 extends over about 70% to 95% of the core. The absorbent core 44 preferably has a substantially uniform thickness between about 0.5 mm and about 2.5 mm.

In a preferred embodiment of the invention, the absorbent core 44 comprises between about 75% to 100% cellulose fibers by weight and 0% to 25% superabsorbent polymer by weight. In a particularly preferred embodiment, the first region 70 and the second region have 72 the same identical material composition. Also, preferably, the first region 70 and second region 72 are composed of a single layer of material, that is the first region 70 and second region 72 are not formed by layering two distinct layers one on top of another.

In the particular embodiment of the invention shown in FIG. 4, the first region 70 of the absorbent core 44 is shaped such that a perimeter 76 thereof has first curvilinear first end portion 78 and a second opposed curvilinear end portion 80, each of the end portions being interconnected by opposed arcuate side portions 82 and 84. The first end portion 78 is located on a first side of the transverse centerline and the second end portion 80 is located on an opposite side of the transverse centerline 78. In this manner, the first region 70 is widest at its most distal portions relative to the intersection of the longitudinal centerline 34 and transverse centerline 36 and is most narrow at the intersection of the longitudinal centerline 34 and transverse centerline 36.

Main Body—Cover Layer

The cover layer 42 may be a relatively low density, bulky, high-loft non-woven web material. The cover layer 42 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 42 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transports it away from the body and the point of deposition. Therefore, the cover layer contributes little to the time taken for the napkin to absorb a given quantity of liquid (penetration time).

Advantageously, the fibers that make up the cover layer 42 should not lose there physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the underlying layers of the absorbent article. Thus, the cover layer 42 is advantageously wettable, hydrophilic and porous. When composed of synthetic hydrophobic fibers such as polyester or bi-component fibers, the cover layer 42 may be treated with a surfactant to impart the desired degree of wettability.

In one preferred embodiment of the present invention the cover is made from a 25 gsm thermal bonded polypropylene fiber nonwoven of the type commercially available from Polystar Company, Salvador, BA, Brazil, commercially known as Multidenier Telão 25 cover.

Alternatively, the cover layer 42 can also be made of polymer film having large pores. Because of such high porosity, the film accomplishes the function of quickly transferring body fluid to the underlying layers of the absorbent article. A suitable cover material of this type is commercially found on the STAYFREE Dry Max Ultrathin product distributed by the Personal Products Company Division of McNeil-PPC, Inc., Skillman, N.J.

The cover layer 42 may be embossed to the remainder of the absorbent core 44 in order to aid in promoting hydrophilicity by fusing the cover to the next layer. Such fusion may be effected locally, at a plurality of sites or over the entire contact surface of cover layer 42 and absorbent core 44. Alternatively, the cover layer 42 may be attached to the absorbent core 44 by other means such as by adhesion.

Main Body—Transfer Layer

Adjacent to the cover layer 42 on its inner side and bonded to the cover layer 42 is the transfer layer 43. The transfer layer 43 provides the means of receiving body fluid from the cover layer 42 and holding it until the underlying absorbent core 44 has an opportunity to absorb the fluid, and therefore acts as a fluid transfer or acquisition layer. The transfer layer 43 is, preferably, more dense than and has a larger proportion of smaller pores than the cover layer 42. These attributes allow the transfer layer 43 to contain body fluid and hold it away from the outer side of the cover layer 42, thereby preventing the fluid from rewetting the cover layer 42 and its surface. However, the transfer layer is, preferably, not so dense as to prevent the passage of the fluid through the layer 43 into the underlying absorbent core 44.

The transfer layer 43 be composed of fibrous materials, such as wood pulp, polyester, rayon, flexible foam, or the like, or combinations thereof. The transfer layer 43 may also comprise thermoplastic fibers for the purpose of stabilizing the layer and maintaining its structural integrity. The transfer layer 43 may be treated with surfactant on one or both sides in order to increase its wettability, although generally the transfer layer 43 is relatively hydrophilic and may not require treatment. The transfer layer 43 is preferably bonded or adhered on both sides to the adjacent layers, i.e. the cover layer 42 and the underlying absorbent core 44.

Materials particularly suitable for use in the first absorbent layer 43, which the inventors have found contribute to reducing the rewet potential have a density in the range of about 0.04 to 0.10 g/cc, a basis weight in the range from about 60 to 150 gsm and a thickness in the range of about 1 to 3 mm. Examples of suitable materials for the transfer layer are through air bonded pulp sold by Buckeye of Memphis, Tenn., under the designation VIZORB 3008, which has a basis weight of 110 gsm, VIZORB 3042, which has a basis weight of 100 gsm, VIZORB 3010, which has a basis weight of 90 gsm and others.

Main Body—Absorbent Core

In one preferred embodiment of the invention, the absorbent core 44 is a blend or mixture of cellulosic fibers and superabsorbent disposed therein. Cellulosic fibers that can be used in the absorbent core 44 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. The flexibility of the material may also be improved by mechanically working the material or tenderizing the material.

The absorbent core 44 can contain any superabsorbent polymer (SAP), which are well known in the art. For the purposes of the present invention, the term "superabsorbent polymer" (or "SAP") refers to materials, which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

In one preferred embodiment of the invention the absorbent core 44 includes between 50% and 100% cellulose pulp by weight and 0% and 50% superabsorbent polymer by weight.

In one specific example of the invention, the absorbent core 44 is constructed from 89% cellulose fluff pulp by weight, commercially available as Golden Isles Fluff Pulp 420#HD 7% Moisture, from GP Cellulose, Brunswick, Ga., USA, mixed with 11% superabsorbent polymer commercially available as Aqua Keep SA70N from Sumitomo Seika Chemicals Co., Ltd., Osaka, Japan.

Method of Making the Absorbent Core

A description of the method of making the absorbent core according to the present invention will now be provided with reference to FIGS. 8-12 which depicts an apparatus 200 for making the absorbent core structure according to the present invention. The pulp used to form the absorbent core 44 is a bleached softwood pulp, produced by a Kraft process. The pulp is provided by the manufacturer as a pulp board 202 in rolled form, the roll identified by the reference numeral 204 in FIG. 8. The pulp board 202 is conveyed from the roll 204 to a device 206 for grinding the pulp board 202 into fibrous pulp 205. The fibrous pulp 205 is released from the grinding device 206 into a chamber 208 for holding the fibrous pulp 205. The apparatus 200 may further optionally include a device 207 for introducing superabsorbent polymer into the chamber 208 to thereby form a fibrous pulp and superabsorbent mixture. Any conventional device suitable for this purpose, and known to those of skill in the art, may be used for introducing the superabsorbent into the chamber 208.

Figure 8:
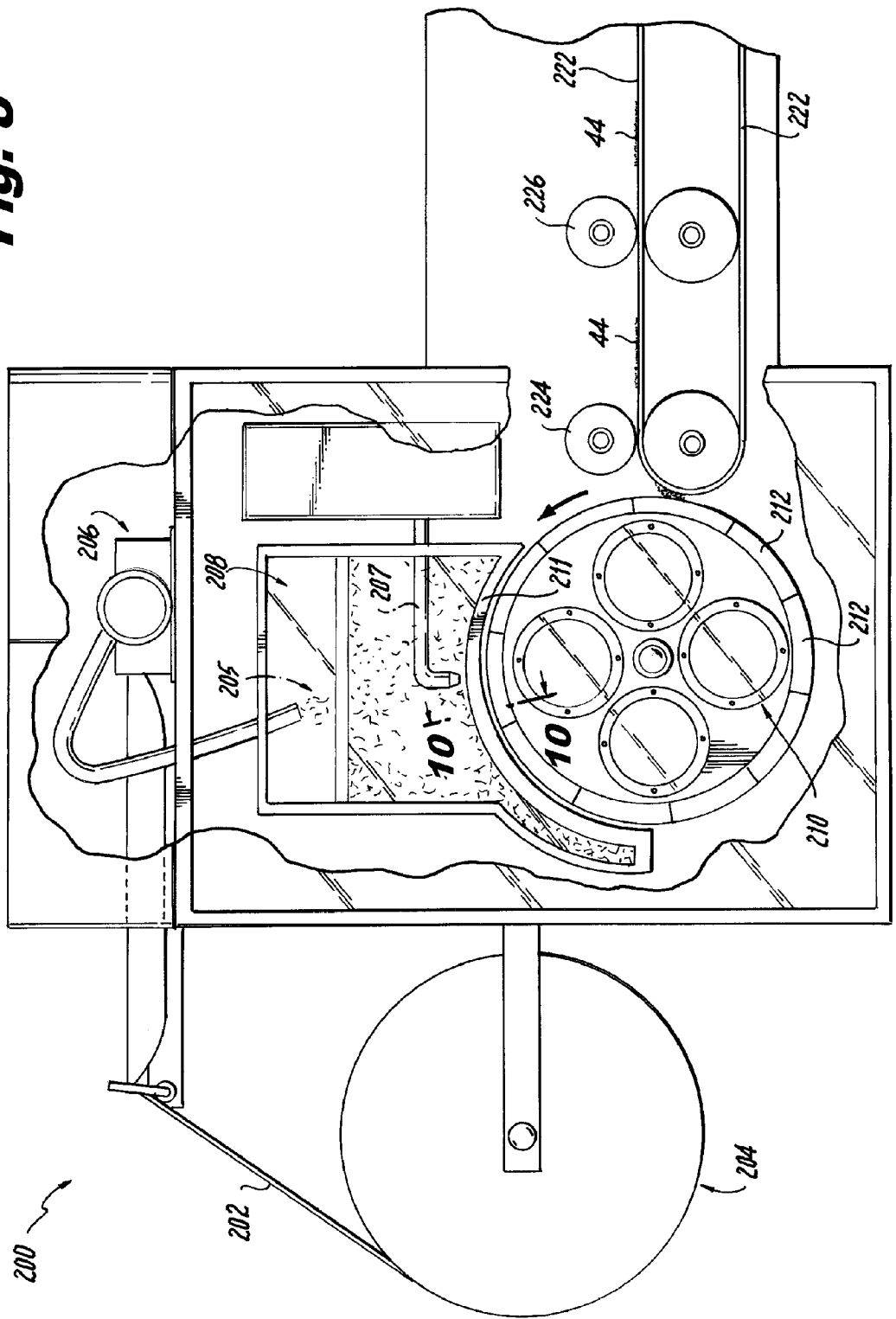
FIG. 8 is a schematic view showing an apparatus for making the core layer shown in FIGS. 3-7.
Figure 9:
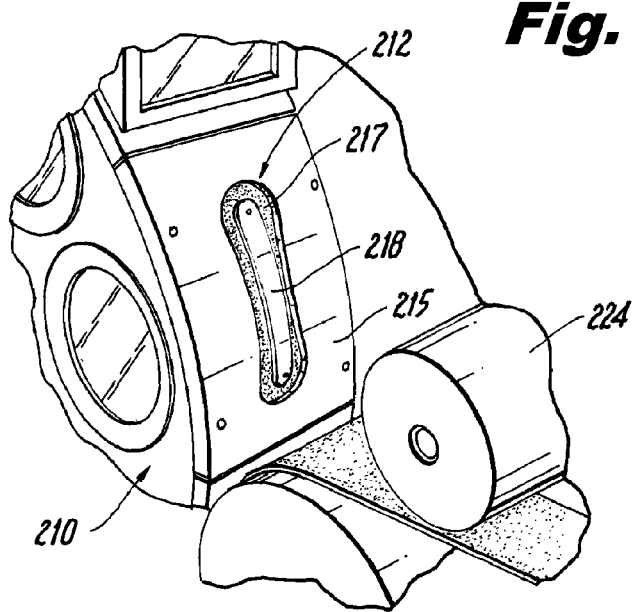
FIG. 9 is a detailed perspective view of a portion of the apparatus shown in FIG. 8.
Figure 10:
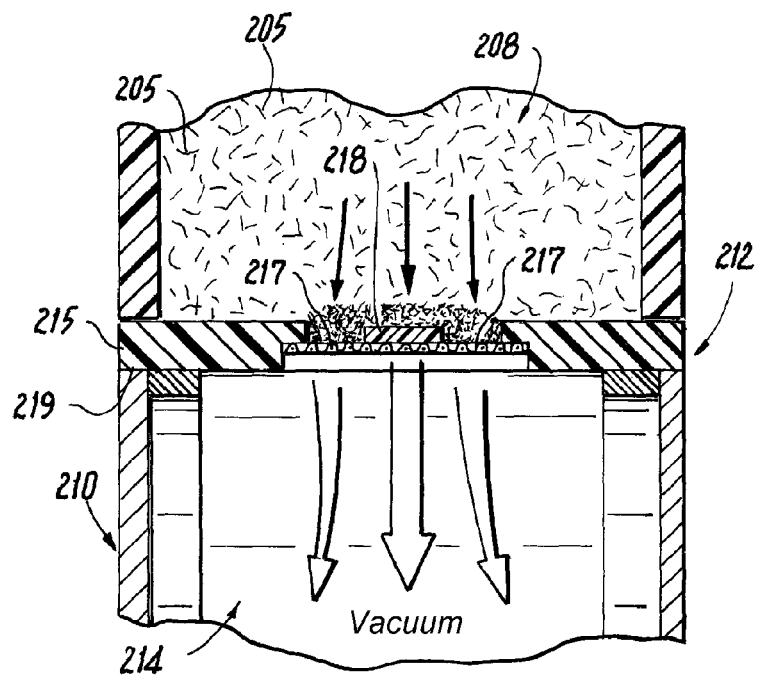
FIG. 10 is a sectional view of the apparatus shown in FIG. 8 taken along line 10-10 thereof.

The chamber 208 has a partially open bottom portion 211 that communicates with a rotating forming drum 210. The rotating forming drum 210 has a plurality of molds 212 mounted thereto. As the forming drum 210 rotates, each of the molds 212 are sequentially arranged in communication with the open portion 211 of the chamber 208 to thereby receive fibrous pulp 205 from the chamber 208. In FIG. 8, the forming drum 210 rotates in a counterclockwise manner during operation of the apparatus 200. As shown in FIG. 10, the forming drum 210 includes a portion 214 that is under vacuum. As shown in FIGS. 9 and 10, the mold 212 includes a porous screen 217 structure in the shape of the second region 72 of the core 44. As the mold 212 passes over portion 214 of the forming drum 210 the vacuum functions to draw the fibrous pulp 205 from the chamber 208 into the mold 212 by drawing air through the porous screen 217 of the mold 212.

As shown in detail in FIG. 10, the mold 212 includes a nonporous mounting plate portion 215 that surrounds the porous screen 217 portion of the mold 212. As best seen in FIG. 10, the mounting plate portion 214 of the mold 212 is mounted to the periphery 219 of the forming drum 210, thereby enabling each of the molds 212 to rotate with the rotating forming drum 210. The porous screen 217 portion of the mold 212 is arranged in the shape of the second region 72 of the core 44. The mold 212 further includes a nonporous central portion 218 in the shape of the first region 70. The nonporous central portion 218 has a height that is less than the height of the mounting plate portion 214. The structure of the mold 212 described above, during use, causes a greater amount of fibrous pulp 205 to be drawn into the porous screen 217 portion of the mold 212 relative to the amount of fibrous pulp 205 drawn into the nonporous central portion 218.

Figure 11:
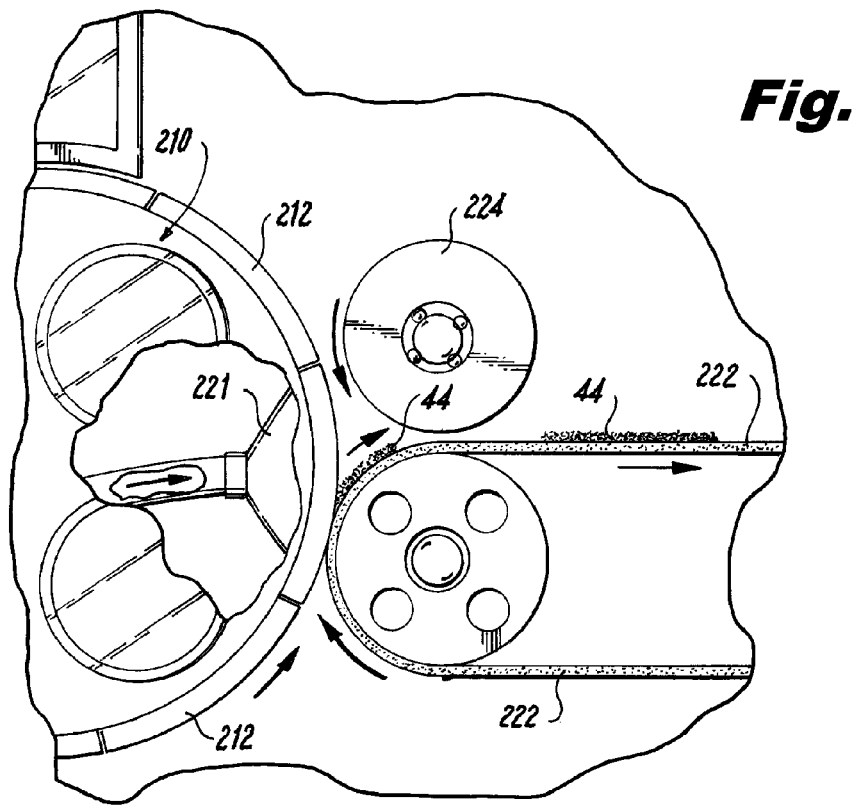
FIG. 11 is a detailed elevation view of a portion of the apparatus shown in FIG. 8.
Figure 12:
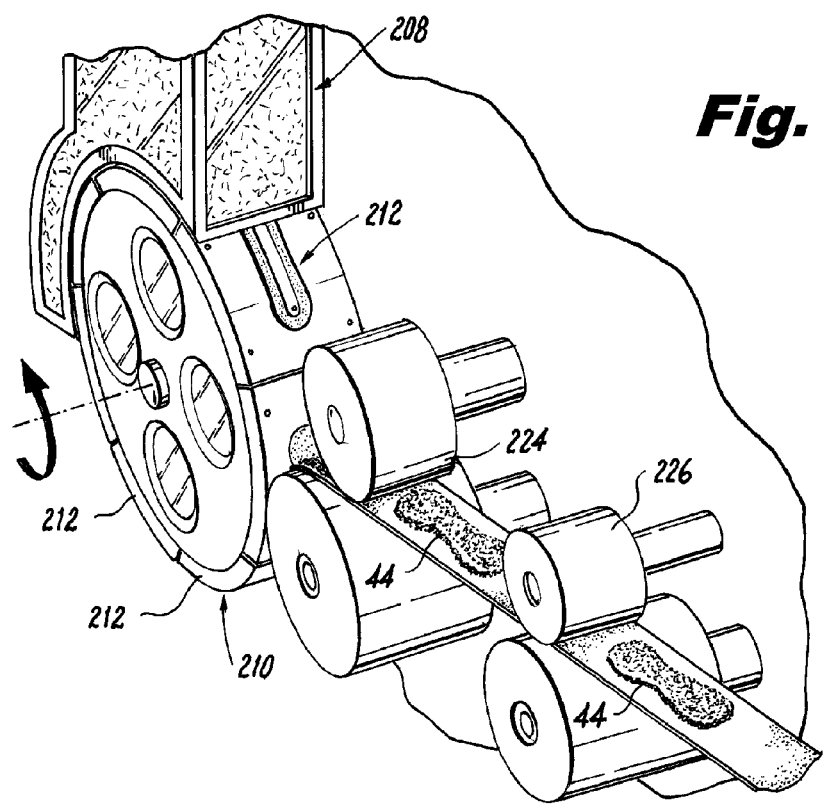
FIG. 12 is a detailed perspective view of a portion of the apparatus shown in FIG. 8.

After the mold 212 is rotated under the partially open bottom portion 211 of the chamber 208, the mold 212 is further rotated by the rotating forming drum 210. As shown in FIG. 11, the rotating forming drum 210 includes a portion 221 that expels air outwardly from within the drum 210. The portion 221 of the drum 210 functions to expel the core 44 structure formed within the mold 212 onto a belt 222. The belt 222 functions to convey the core 44 to a first calendar roll 224. The calendar roll 224 functions to reduce the thickness of the core 44. As shown in FIG. 12, the core 44 is then further conveyed by the belt 222 to a second calendar roll 226 that functions to further reduce the thickness of the core 44 to its final thickness. As shown in FIG. 12, after passing through the second calendar roll 226, the first 70 and second 72 regions of the core 44 have a uniform thickness but have different basis weights.

Main Body—Barrier Layer

Underlying the absorbent core 44 is a barrier layer 50 comprising liquid-impervious film material so as to prevent liquid that is entrapped in the absorbent core 44 from egressing the sanitary napkin and staining the wearer's undergarment. The barrier layer 50 is preferably made of polymeric film, although it may be made of liquid impervious, air-permeable material such as repellent-treated non-woven or micropore films or foams.

The barrier layer may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 42 and the barrier layer 50 are joined along their marginal portions so as to form an enclosure or flange seal that maintains the absorbent core 44 captive. The joint may be made by means of adhesives, heat-bonding, ultrasonic bonding, radio frequency sealing, mechanical crimping, and the like and combinations thereof.

Positioning adhesive may be applied to a garment facing side of the barrier layer for securing the napkin 10 to a garment during use. The positioning adhesive may be covered with removable release paper so that the positioning adhesive is covered by the removable release paper prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

The absorbent article of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof, hot melt adhesives based on suitable block copolymers—suitable block copolymers for use in the invention include linear or radial co-polymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Where adhesive is used, a release strip may be applied to protect the adhesive on the absorbent article prior to attaching the absorbent article to the crotch. The release strip can be formed from any suitable sheet-like material adheres with sufficient tenacity to the adhesive to remain in place prior to use but which can be readily removed when the absorbent article is to be used. Optionally, a coating may be applied to release strip to improve the ease of removabilty of the release strip from the adhesive. Any coating capable of achieving this result may be used, e.g., silicone.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like materials, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated by the present invention are asymmetrical and symmetrical absorbent articles having parallel longitudinal edges, dog bone- or peanut-shaped, as well as articles having a tapered construction for use with thong-style undergarments. From the foregoing description, one skilled in the art can ascertain the essential characteristics of this invention, and without departing from the spirit and scope thereof, can make various changes and modifications. Embodiments set forth by way of illustration are not intended as limitations on the variations possible in practicing the present invention.

Test Procedures

Absorbent articles according to the present invention have a unique combination of functional properties, in particular articles according to the present invention are particularly flexible in the transverse direction and also provide superior fluid handling characteristics. A number of test procedures are described below that highlight the functional properties of absorbent articles according to the present invention. Prior to conducting any of the described test procedures described below the test product should be conditioned for two hours at 21+/−1° C. and 50+/−2% humidity.

Procedure for Measuring the Thickness of an Absorbent Article

Preferred embodiments of the present invention relate to "ultra-thin" sanitary napkins. "Ultra-thin" sanitary napkins as defined herein are those sanitary napkins that have a thickness of less than 5 mm and more preferably less than 4 mm according to the test method set forth herein.

The apparatus required to measure the thickness of an absorbent article is a footed dial (thickness) gauge with stand, available from Ames, with a 2" (5.08 cm) diameter foot at a pressure of 0.07 psig and a readout accurate to 0.001" (0.00254 cm). A digital type apparatus is preferred. If the absorbent article sample is individually folded and wrapped, the sample is unwrapped and carefully flattened by hand. The release paper is removed from the product sample and it is repositioned back gently across the positioning adhesive lines so as not to compress the sample, ensuring that the release paper lies flat across the sample. Flaps (if any) and release paper are not considered when taking the thickness.

The foot of the gauge is raised and the product sample is placed on the anvil such that the foot of the gauge is approximately centered over the intersection of the longitudinally extending centerline and transversely extending centerline on the product sample. When lowering the foot, care must be taken to prevent the foot from dropping onto the sample or from undue force being applied. A load of 0.07 p.s.i.g. is applied to the sample and the read out is allowed to stabilize for approximately 5 seconds. The thickness reading is then taken. This procedure is repeated for at least five product samples and the average thickness is then calculated.

Procedure for Measuring Rewet Potential

The rewet potential is a measure of the ability of a napkin or other article to hold liquid within its structure when the napkin contains a relatively large quantity of liquid and is subjected to external mechanical pressure. Absorbent articles according to the present invention preferably have a rewet value of less than 1.0 g, more preferably less than 0.5 g, and most preferably less than 0.25 g. The rewet potential is determined and defined by the following procedure.

Figure 16:
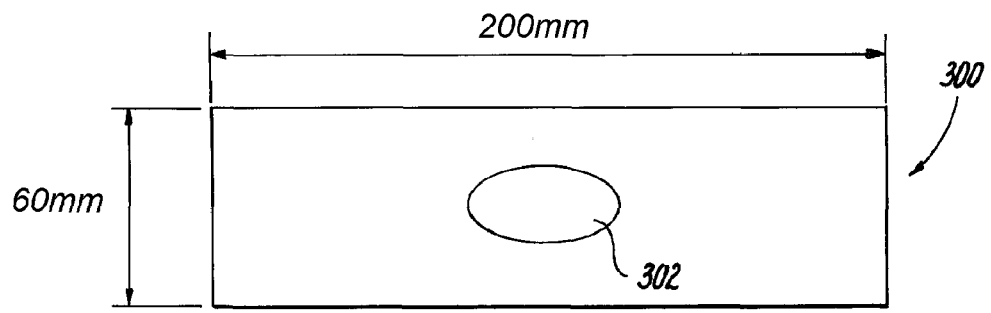
FIG. 16 is a top elevation view of a test plate used to conduct the Rewet Potential Test Method described herein.

The instruments required for the Rewet Potential test include an orifice plate (described below), a quantity of 3 inch×4 inch rectangles of Whatman #1 filter paper (Whatman Inc., Clifton, N.J.), a calibrated electronic repeater pipette (HandyStep Electronic Repeating Pipet, Brandtech) with a 50 mL combi-syringe (or combi-tip) capable of delivering 5-10 mL at a rate of approximately 4 mL/s, and a weighing machine or balance capable of weighing to an accuracy of +/−0.01 g, a standard weight of 2.22 kg (4.8 pounds) having dimensions 5.1 cm (2 inches) by 10.2 cm (4.0 inches) by approximately 5.4 cm (2.13 inches) which applies a pressure of 4.14 kPa (0.6 psi) over the 5.1 cm by 10.2 cm (2 inches by 4 inches) surface. The orifice plate 300, as shown in FIG. 16, consists of a 7.6 cm×25.4 cm plate of 1.3 cm thick polycarbonate with an elliptical orifice 302 in its center. The elliptical orifice 302 measures 3.8 cm along its major axis and 1.9 cm along its minor axis. The longitudinal axis of the elliptical orifice 302 is arranged parallel to the longitudinal axis of the product to be tested.

A synthetic test fluid used in replacement of human menses due to its ease in preparation and accessibility of the ingredients. The fluid is prepared by dissolving each of the following components into distilled water. Care should be taken to ensure that components are well dissolved. A rotating blade mixer or a magnetic stirrer should be used for mixing the components. In a large enough container, add the following components, making sure that the component is dissolved before adding the next one:

| Quantity/ 1 L | Reagent | Grade, purity | Supplier | Catalog no. |
|---|---|---|---|---|
| 9.0 g | sodium chloride | ACS reagent 99+% | Sigma-Aldrich | 223514 |

-continued

| Quantity/ 1 L | Reagent | Grade, purity | Supplier | Catalog no. |
|---|---|---|---|---|
| 490.5 g | distilled water | N/AP | N/AP | N/AP |
| 10 g | 2-phenoxyethanol | puriss. 99.0% | Sigma-Aldrich (Fluka) | 77699 |
| 0.5 g | FD&C Red #40 | Food | A&C | C3465 |
| 490.5 g | glycerol | ACS reagent 99.5% | Sigma-Aldrich | G7893 |

A 50 mL combi-syringe (or combi-tip), placed on a repeater pipette, is filled with the test fluid, positioned vertically and the tip placed approximately 1 inch from the surface of the product and above the center of the elliptical hole of the plate. The article should be arranged such that the intersection of the longitudinally extending and transversely extending centerlines is positioned in the center of the hole. Then, 7 mL of test fluid is insulted to the article at a rate of approximately 4 mL/s.

After the test fluid is applied within the orifice plate 300 and as soon as the cover layer of the napkin first appears through the top surface of the fluid, the stopwatch is started and an interval of 5 minutes is measured.

After 5 minutes have elapsed, the orifice plate 300 is removed and the napkin is positioned on a hard level surface with the cover layer facing upwards.

A fifteen (15) layer stack of the pre-weighed filter paper is placed on and centered over the wetted area and the standard 2.22 kg weight is placed on top of the filter paper. The filter paper and the weight are arranged over the absorbent article such that they are centered over the area to which the fluid was applied. The filter paper and the weight are arranged such that their longer dimensions are aligned with the longitudinal direction of the product. Immediately after placing the paper and weight on the product, the stopwatch is started and after a 3 minute interval has elapsed the standard weight and filter paper are quickly removed. The wet weight of the filter paper is measured and recorded to the nearest 0.01 grams. The rewet value is then calculated as the difference in grams between the weight of the wet 15 layers of filter paper and the dry 15 layers of filter paper.

The measurement should have at least five replicates and, if necessary, the weight is wiped clean before each run. The average rewet value is then calculated from the five measured values and recorded as the average rewet value.

Procedure for Measuring Lateral Rigidity

Absorbent articles according to the present invention preferably have a relatively low lateral rigidity thereby promoting comfort during use. In particular, articles according to the present invention preferably have a lateral rigidity of less than 1000 g, more preferably less than 900 g, and most preferably less than 875 g.

Figure 13:
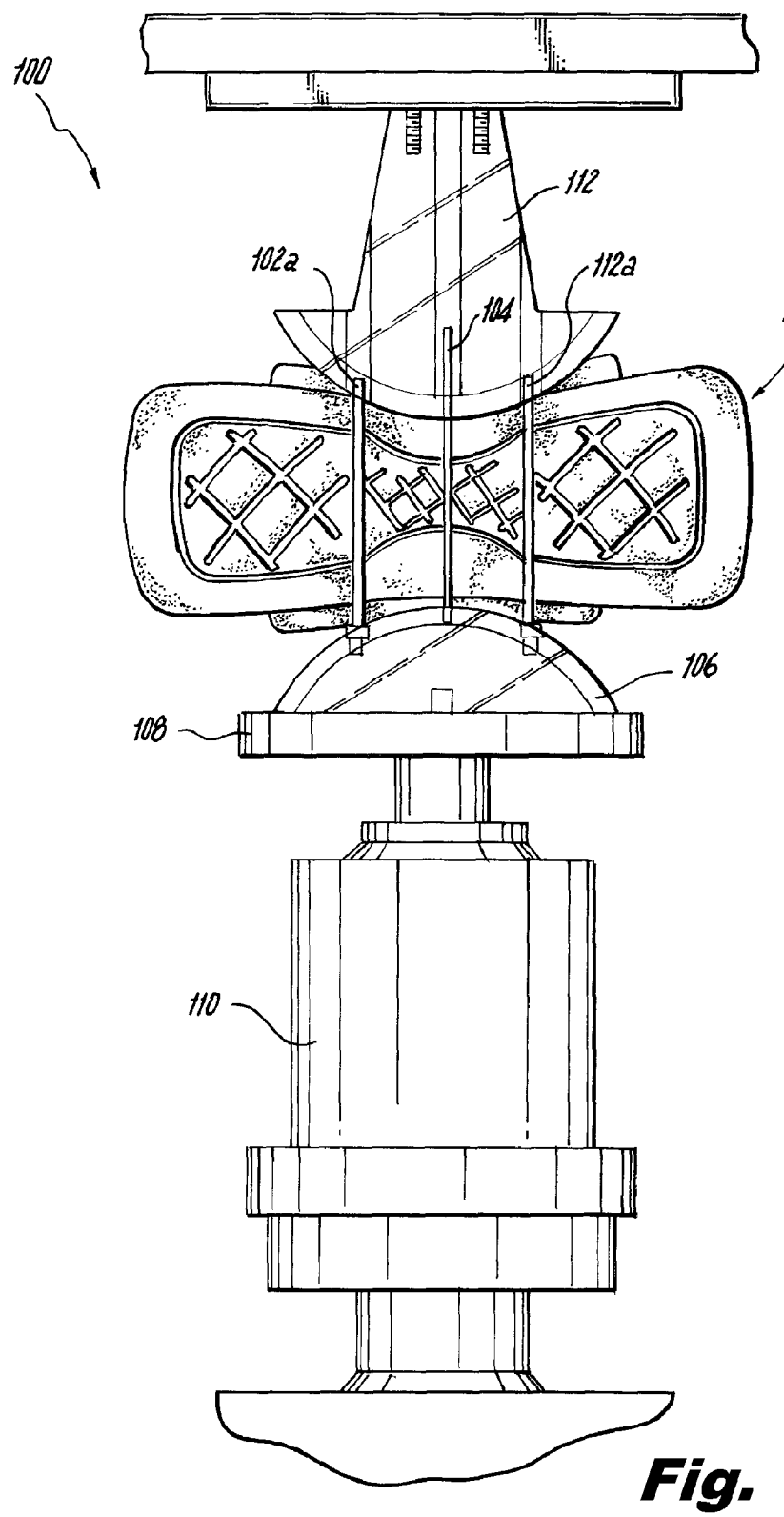
FIG. 13 is a front elevation view of an apparatus for measuring lateral rigidity of an absorbent article together with an absorbent article mounted in the device for testing.
Figures 14, 15:
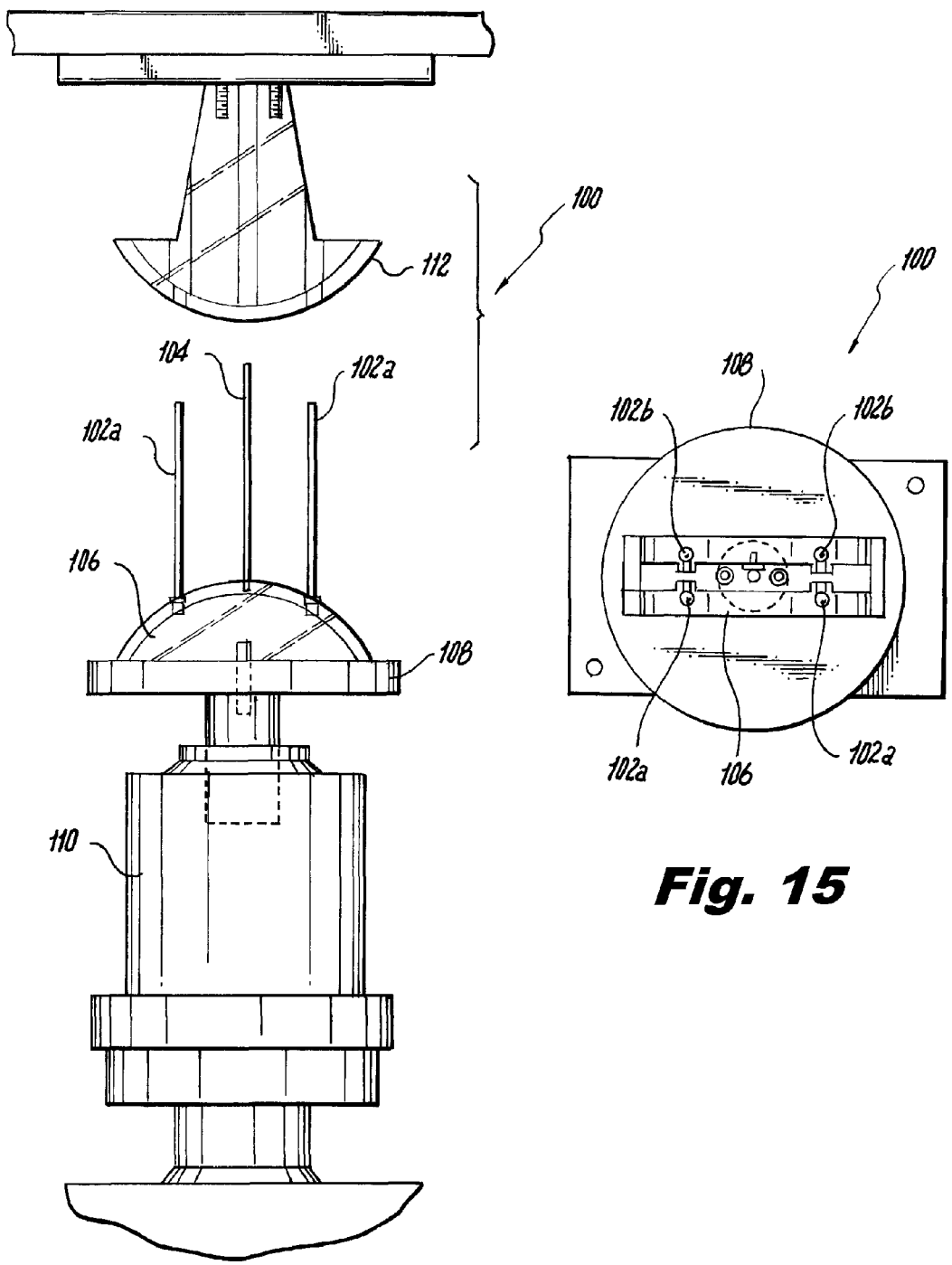
FIG. 14 is a front elevation view of the apparatus shown in FIG. 13.
FIG. 15 is a top elevation view of the apparatus shown in FIG. 13.

A method for measuring the lateral rigidity of an absorbent article is described below. The apparatus 100 required for this measurement is illustrated in FIGS. 13-15. The apparatus 100 includes two front metal rods 102a (diameter=4.4 mm, length=102.2 mm), two rear metal rods 102b (diameter=4.4 mm, length=102.2 mm), and one central metal rod 104 (diameter=2.4 mm, height=92.1 mm) mounted on a first Plexiglass arc-shaped plate 106 (diameter=139.7 mm and height=37.9 mm), which serves to hold the sanitary napkin 10. The napkin 10 (or other absorbent article to be tested) should be arranged such that the intersection of the longitudinally extending centerline 15 and transversely extending centerline 17 is arranged in alignment with the central metal rod 104.

The two front metal rods 102a are spaced from one another by a distance of 31.8 mm as measured from the center of one rod to the center of the other rod. The two rear metal rods 102b are also spaced from one another by a distance of 31.8 mm as measured from the center of one rod to the center of the other rod. The distance between corresponding front 102a and rear 102b rods, i.e. the front and rear rods that are in front to back alignment, is 12.7 mm.

The plate 106 is mounted on the base 108 of an inverted compression load cell 110. A second Plexiglas arc-shaped plate 112 (diameter=139.7 mm and height=37.9 mm) is placed upside down on the top part of the inverted compression cell and used to compress the napkin 10 in the transverse direction thereof. The load cell has a range of about 0.0 to about 2000.0 g and is used on an actuator and more specifically on an Instron Model No. 1123 (Instron Engineering Corporation, Canton, Mass.).

Before starting the measurement, the napkin is removed from the packaging and unfolded. The release paper is removed and talc powder is sprinkled over the adhesive strips. Using a ruler and the central rod as a guide, the initial position of the compression cell is adjusted so that the distance between the surfaces of the plates 106 and 112 is 7.62 cm (3 inches). The napkin 10 is placed between the rods 102a, 102b, and 104, as shown in the FIG. 7. The actuator is set so that during the compression cycle, it will move down by 5.08 cm at a speed of 50 cm/min. The peak force (g) measured during the first compression cycle is recorded as the lateral rigidity of the sample. This procedure is repeated with five different product samples and an average value is calculated.

EXAMPLES

Specific inventive examples of the present invention are described below. Comparative examples are also described below. Each of the inventive and comparative examples were subjected to the test methods described above and the results of such tests are summarized in the Table set forth below.

Inventive Example #1

An example of an ultrathin sanitary napkin according to the invention was constructed as follows. The body facing cover layer was constructed from a 25 gsm hot through air bonded nonwoven material constructed from 100% hydrophilic polypropylene fibers, commercially available form Polystar Company, Salvador, Brazil under the commercially name of Multidenier Telão 25 cover. A 100 gsm transfer layer was arranged below the cover layer, the transfer layer was formed from through air bonded pulp sold by Buckeye of Memphis, Tenn., under the designation VIZORB 3042. An absorbent core was arranged below the transfer layer and was formed by the process described herein with reference to FIGS. 8-12. The absorbent core had a first region with a surface area of 9700 mm² and second region with a surface area of 2100 mm². The first region had a basis weight of 300 gsm and the second region had a basis weight of 150 gsm. The absorbent core had a composition of 89% by weight of pulp and 11% by weight of superabsorbent polymer. The pulp was Golden Isles Fluff Pulp 420#HD 7% Moisture, commercially available from GP Cellulose, Brunswick, Ga., USA. The superabsorbent polymer was Aqua Keep SA70N commercially available from Sumitomo Seika Chemicals Co., Ltd., Osaka, Japan. A barrier layer was arranged below the core and was formed from a 24 gsm polyethylene (PE 24 gsm) film commercially available from Clopay do Brasil, São Paulo, SP, Brazil. Each of the layers of the sanitary napkin were adhered to one another using a conventional hot melt adhesive.

Comparative Example #1

Comparative Example #1 was constructed in the same manner as Inventive Example #1 except that the absorbent core of Inventive Example #1 was replaced with a core having the same material composition as the core described with respect to Inventive Example #1 but having a uniform basis weight of 300 gsm.

Inventive Example #2

Inventive Example #2 was constructed in the same manner as Inventive Example #1 except that the cover layer thereof was replaced by the cover layer found on the STAYFREE Ultrathin Drymax product distributed by McNeil-PPC, Inc.

Comparative Example #2

Comparative Example #2 was constructed in the same manner as Inventive Example #2 except that the core layer was replaced with a core having the same material composition as the core described with respect to Inventive Example #1 but having a uniform basis weight of 300 gsm.

Each of the inventive example and comparative example were tested according to the test methods set forth herein and the results of such testing are set forth in Table #1 below.

TABLE #1

| | Thickness (mm) | Rewet (g) | Lateral Rigidity (g) |
|---|---|---|---|
| Inventive Example #1 | 2.91 | 0.03 | 921.5 |
| Comparative Example #1 | 3.25 | 0.03 | 1224.7 |
| Inventive Example #2 | 3.11 | 0.16 | 854.7 |
| Comparative Example #2 | 2.89 | 0.03 | 1193.1 |

Applications of the absorbent article according to the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. An absorbent article comprising:
   a liquid pervious cover layer;
   a liquid impervious barrier layer;
   an absorbent core arranged between the cover layer and barrier layer;
   a transfer layer arranged between the cover layer and the core;
   a longitudinal centerline;
   a transverse centerline;
   wherein the absorbent core has a first region and second region concentrically surrounding the first region, the first region having a first basis weight and the second region having a second basis weight, the first basis weight being less than the second basis weight, the first basis weight being in the range of between 7.5 gsm and 385 gsm and the second basis weight being in the range of between 150 and 450, wherein the basis weight of the first region is about 5% to about 85% the basis weight of the second region; and wherein the first region includes a first end portion located on a first side of the transverse centerline and a second end portion located on an opposite side of the transverse centerline.

2. The absorbent article according to claim 1, wherein the first region extends along the longitudinal centerline of the absorbent article and is symmetrically arranged with respect to the longitudinal centerline, the first region extending over about 5% to 30% the surface area of the core and the second region extending over about 70% to 95% of the core.

3. The absorbent article according to claim 2, wherein the absorbent core comprises between about 75% to 100% cellulose fibers by weight and 0% to 25% superabsorbent by weight.

4. The absorbent article according to claim 3, wherein the absorbent article has a thickness less than 5 mm, a rewet value of less than 1 g, and a lateral stiffness of less than 1000 g.

5. The absorbent article according to claim 1, wherein the first region extends along the longitudinal centerline.

6. The absorbent article according to claim 5, wherein the first end portion and the second end portion are interconnected by a first and second side portion.

7. The absorbent article according to claim 6, wherein the first region is structured and arranged such that it is widest at its most distal portions relative to the intersection of the longitudinal centerline and transverse centerline and is most narrow at the intersection of the longitudinal centerline and transverse centerline.

* * * * *